United States Patent
Guo et al.

(10) Patent No.: US 11,766,406 B2
(45) Date of Patent: Sep. 26, 2023

(54) SOFT GELATIN CAPSULES CONTAINING A MIXTURE OF ANALGESICS AND DECONGESTANTS, EXPECTORANTS, ANTITUSSIVES AND/OR ANTIHISTAMINES

(71) Applicant: PuraCap Pharmaceutical LLC, Iselin, NJ (US)

(72) Inventors: Dahai Guo, Belle Mead, NJ (US); Minh Tran, Secaucus, NJ (US); Zhang Julia Zhang, Scotch Plains, NJ (US)

(73) Assignee: PuraCap Pharmaceutical LLC, Iselin, NJ (US)

( * ) Notice: Subject to any disclaimer, the term of this patent is extended or adjusted under 35 U.S.C. 154(b) by 14 days.

(21) Appl. No.: 17/692,521

(22) Filed: Mar. 11, 2022

(65) Prior Publication Data

US 2022/0265561 A1 Aug. 25, 2022

Related U.S. Application Data

(63) Continuation of application No. 15/762,952, filed as application No. PCT/US2016/054052 on Sep. 28, 2016, now abandoned.

(60) Provisional application No. 62/233,638, filed on Sep. 28, 2015.

(51) Int. Cl.
| | |
|---|---|
| *A61K 9/48* | (2006.01) |
| *A61K 47/10* | (2017.01) |
| *A61K 47/32* | (2006.01) |
| *A61K 31/167* | (2006.01) |
| *A61K 31/09* | (2006.01) |
| *A61K 31/137* | (2006.01) |
| *A61K 31/485* | (2006.01) |

(52) U.S. Cl.
CPC .......... *A61K 9/4866* (2013.01); *A61K 9/4825* (2013.01); *A61K 9/4833* (2013.01); *A61K 31/167* (2013.01); *A61K 47/10* (2013.01); *A61K 47/32* (2013.01); *A61K 31/09* (2013.01); *A61K 31/137* (2013.01); *A61K 31/485* (2013.01); *A61K 2300/00* (2013.01)

(58) Field of Classification Search
CPC .... A61K 9/4833; A61K 31/167; A61K 47/10; A61K 2300/00
See application file for complete search history.

(56) References Cited

U.S. PATENT DOCUMENTS

| 5,510,389 A * | 4/1996 | Dhabhar .............. A61K 31/167 |
| | | 514/629 |
| 2001/0007568 A1 | 7/2001 | Morris |
| 2013/0261189 A1 | 10/2013 | Rashid et al. |
| 2014/0243364 A1 | 8/2014 | Agisim et al. |

FOREIGN PATENT DOCUMENTS

| CN | 105007891 A | 10/2015 |
| WO | 2007125501 A2 | 11/2007 |
| WO | 2013090460 A1 | 6/2013 |

OTHER PUBLICATIONS

Drugs.com; DayQuil Sever Cold & Flu; published: Oct. 23, 2014; obtained online on Mar. 17, 2020.
Ashland, "PVP Polyvinylpyrrolidone polymers", published online: Mar. 29, 2017. (Year: 2017).

\* cited by examiner

*Primary Examiner* — Genevieve S Alley
(74) *Attorney, Agent, or Firm* — Fox Rothschild LLP

(57) ABSTRACT

Clear bioavailable liquid softgel fill compositions comprising a) at least one analgesic and one or more of decongestants, expectorants, antitussives and/or antihistamines; b) a matrix comprising a pharmaceutically acceptable poly(alkylene glycol) and a pharmaceutically acceptable alkylene glycol; c) a solubilizing agent comprising a pharmaceutically acceptable polymeric solubilizing agent and water are disclosed. Also disclosed are methods for the preparation of such clear fill compositions, and softgel capsules containing the clear bioavailable liquid fill composition.

3 Claims, 1 Drawing Sheet

SOFT GELATIN CAPSULES CONTAINING A MIXTURE OF ANALGESICS AND DECONGESTANTS, EXPECTORANTS, ANTITUSSIVES AND/OR ANTIHISTAMINES

CROSS-REFERENCE TO RELATED APPLICATIONS

This application is a continuation of Ser. No. 15/762,952, filed on Mar. 23, 2018, which is a U.S. national phase of PCT/US16/54052, filed on Sep. 28, 2016, which claims the benefit of priority pursuant to 35 U.S.C. § 119(e) of U.S. Provisional Patent Application No. 62/233,638, filed on Sep. 28, 2015, the disclosure of which is incorporated herein by reference in its entirety.

FIELD OF THE DISCLOSED SUBJECT MATTER

The presently disclosed subject matter relates to bioavailable fill compositions containing an analgesic and one or more of a decongestant, expectorant, antitussive and/or antihistamine; soft gelatin capsules filled with the bioavailable fill compositions; and methods of making same.

BACKGROUND

Combinations of various medications are frequently taken by patients suffering from colds or other viral or bacterial infections, especially respiratory infections. Combination medicines in a unitary formulation are sought for their convenience. For example, a highly concentrated solution of the medications allows the entire combination to be encapsulated in a reasonable small sized (0.2-1.8 mL) clear softgel capsule for easy swallowing. It also enhances the bioavailability of the medications. However, some medications such as acetaminophen, tend to recrystallize in such a solution. There is a need for clear, highly concentrated formulations suitable for encapsulation in softgel and related preparation methods.

SUMMARY OF THE DISCLOSED SUBJECT MATTER

A new formulation providing desirable combinations of active ingredients, particularly a combination of at least one analgesic with one or more of decongestants, expectorants, antitussives and/or antihistamines in a unitary formulation is provided herein. This formulation provides convenience to the patient and aids compliance in taking the medications. The formulation can be free of any ionizing agent; namely, a compound or agent (such as alkali metal ions, i.e., lithium, sodium, potassium, rubidium, and cesium cations) capable of ionizing an active ingredient (e.g., acetaminophen here) in a solution.

An overall approach to formulating the combination of the active ingredients (AIs) is to prepare a fill composition and encapsulate it with a soft gelatin capsule (softgel), specifically solubilizing the AIs in a suitable matrix comprising a polymeric solubilizing agent and water in an alkylene glycol and poly(alkylene glycol) vehicle.

The solubilizing matrix comprises two parts. Part A is a hydrophilic mixture of a pharmaceutically acceptable alkylene glycol, such as propylene glycol and a pharmaceutically acceptable poly(alkylene glycol), such as a polyethylene glycol (PEG). Part B is a mixture of a pharmaceutically acceptable solubilizing polymer, such as a polyvinylpyrrolidone (povidone) and water. Parts A and B are combined to form the solubilizing matrix, and the active ingredients are added to this solubilizing matrix to form the fill composition as clear solutions.

The fill composition of the invention can then be encapsulated into soft gelatin capsules of the invention.

One aspect of the invention provides a bioavailable liquid softgel fill composition comprising: (a) active ingredients; (b) a matrix comprising: 20-70 (e.g., 30-70, 40-60, or 45-50) % by weight of a pharmaceutically acceptable poly(alkylene glycol) and 0.5-8% by weight of a pharmaceutically acceptable alkylene glycol; and (c) a solubilizing agent comprising: 1-30% by weight of a pharmaceutically acceptable polymeric solubilizing agent; and 1-10% by weight water, based on the total weight of the composition. The active ingredients comprise one or more of ingredients selected from the group consisting of acetaminophen, dextromethorphan HBr, doxylamine succinate, guaifenesin, and phenylephrine HCl. For example, the bioavailable liquid softgel fill composition can comprise about 10-60% acetaminophen, about 0.3-3% dextromethorphan HBr, 0-2% doxylamine succinate, 0-30% guaifenesin, and 0.1-2% phenylephrine HCl. An additional active ingredient can be chlorpheniramine maleate.

One aspect of the invention is directed to a bioavailable liquid softgel fill composition comprising: a) active ingredients; b) a matrix comprising: bi) 40-55% by weight of a pharmaceutically acceptable poly(alkylene glycol); bii) 1-5% by weight of a pharmaceutically acceptable alkylene glycol; and c) a solubilizing agent comprising: c1) 5-20% by weight of a pharmaceutically acceptable polymeric solubilizing agent; and c2) 1-10% by weight water, based on the total weight of the composition. The active ingredients a) comprise the remainder to 100% by weight of the fill composition. In one embodiment the pharmaceutically acceptable poly(alkylene glycol) is selected from the group consisting of poly(ethylene glycol)s (PEGs); preferably the PEGs are selected from the group consisting of PEG 200, 300, 400, 600, mixtures thereof, and mixtures of these with PEG 800, 1000, 2000, 3000, 4000, 5000, 6000, 7000, or 8000. In one embodiment the pharmaceutically acceptable alkylene glycol is propylene glycol. In one embodiment of the fill composition, the pharmaceutically acceptable polymeric solubilizing agent is a polyvinylpyrrolidone (PVP). In one embodiment the PVP is selected from the group consisting of PVP K12, PVP K17, PVP K30, PVP K60, and PVP K90; preferably the polyvinylpyrrolidone is PVP 12, PVP 17 or PVP 30.

Another aspect of the invention is directed to a method of preparing the above bioavailable liquid softgel fill composition, comprising the steps of: (a) combining the poly(alkylene glycol) and the alkylene glycol in a stainless steel container and heating the mixture to a temperature of 70±10° C. with stirring for a first period of time to obtain a mixture; (b) slowly adding the polymeric solubilizing agent in small quantities into the mixture with stirring and continuing stirring at the same temperature for a second period of time after powder addition is complete; (c) adding water and continuing to mix at the same temperature of (70±10° C.) for a third period of time; (d) adding the active ingredients in small quantities with mixing at the same temperature; (e) continuing to mix for a fifth period of time after powder addition has been completed to obtain the fill composition; and (f) cooling and deaerating the mixture to ambient temperature, providing the liquid softgel fill composition.

Another aspect of the invention is directed to a softgel capsule comprising a soft gelatin capsule filled with the bioavailable liquid softgel fill composition disclosed above. In one embodiment the gelatin of said soft gelatin (softgel) capsule comprises bovine-, avian-, porcine-, marine- or vegetable-based gelatin, or a mixture of two or more thereof. In one embodiment, the softgel capsule further comprises an enteric coating. The enteric coating preferably comprises a controlled release or delayed release polymer. In one embodiment the controlled release polymer is an acid-resistant polymer.

Another aspect of the invention is directed to a bioavailable liquid softgel fill composition consisting essentially of the components as described above.

Yet another aspect of the invention is directed to a bioavailable liquid softgel fill composition consisting essentially of: ai) about 28% by weight of acetaminophen; aii) about 0.9% by weight of dextromethorphan HBr; aiii) about 0.5% by weight of doxylamine succinate; aiv) about 0.5% by weight of phenylephrine HCl; b) a matrix comprising: bi) about 48% by weight of PEG 400; and bii) about 1.3% by weight of propylene glycol; c) a solubilizing agent comprising: ci) about 14% by weight of polyvinylpyrrolidone; and cii) about 6.3% by weight of water; based on the total weight of the composition.

Yet another aspect of the invention is directed to a bioavailable liquid softgel fill composition consisting essentially of: ai) about 23% by weight of acetaminophen; aii) about 0.7% by weight of dextromethorphan HBr; aiii) about 14% by weight of guaifenesin; aiv) about 0.4% by weight of phenylephrine HCl; b) a matrix comprising: bi) about 47% by weight of PEG 400; and bii) about 2% by weight of propylene glycol; c) a solubilizing agent comprising: ci) about 7% by weight of polyvinylpyrrolidone; and cii) about 6% by weight of water; based on the total weight of the composition.

Yet another aspect of the invention is directed to a clear bioavailable liquid softgel fill composition consisting essentially of: ai) about 25% by weight of acetaminophen; aii) about 0.8% by weight of dextromethorphan HBr; aiii) about 15% by weight of guaifenesin; aiv) about 0.4% by weight of phenylephrine HCl; b) a matrix comprising: bi) about 15% by weight of PEG 600 and about 32% by weight of PEG 400; and bii) about 3.8% by weight of propylene glycol; c) a solubilizing agent comprising: ci) about 3% by weight of polyvinylpyrrolidone; and cii) about 5.6% by weight of water; based on the total weight of the composition. This fill composition is clear (See Example 5).

Yet another aspect of the invention is directed to a clear bioavailable liquid softgel fill composition consisting essentially of: ai) about 22.79% by weight of acetaminophen; aii) about 0.74% by weight of dextromethorphan HBr; aiii) about 14.03% by weight of guaifenesin; aiv) about 0.37% by weight of phenylephrine HCl; b) a matrix comprising: bi) about 48.04% by weight of PEG 400; and bii) about 3.51% by weight of propylene glycol; c) a solubilizing agent comprising: ci) about 4.56% by weight of polyvinylpyrrolidone; and cii) about 5.96% by weight of water; based on the total weight of the composition. This fill composition is clear (see Example 6), and remains clear and stable on storage for at least two years.

One embodiment of the above compositions is directed to a softgel capsule comprising a soft gelatin capsule filled with the above bioavailable liquid softgel fill composition. Preferably the polyvinylpyrrolidone is PVP K17.

BRIEF DESCRIPTION OF THE DRAWING

FIG. 1 shows a picture of a sample of the composition of Example 4 after storage for 2 years. During this period of time the sample remained clear.

DETAILED DESCRIPTION OF PREFERRED EMBODIMENTS

This invention provides a clear, liquid pharmaceutical formulation that contains a combination of at least one analgesic with one or more of decongestants, expectorants, antitussives and/or antihistamines. It was unexpected that the formulation can be prepared as a clear liquid and remain clear without recrystallization for an extended period of time (8 days up to 2 years) despite the highly concentrated active ingredients (such as acetaminophen). The formulation is suitable for preparing various oral dosage forms, e.g., soft gel capsule, suspension, solution, syrup, two-piece hard shell capsule, and nasal/oral spray. See Modern Pharmaceutics, Volume 121(2004), edited by Gilbert S. Banker and Christopher T. Rhodes, and references cited therein. See also U.S. Pat. Nos. 8,518,438 and 8,969,416. These documents are hereby incorporated by reference in their entirety. In particular, it may be used to prepare soft gels containing a high dose of the combination in a stable solution.

As used herein, the term "analgesic" designates any of a number of well-known drugs which are commonly used to relieve headaches and to reduce fever. Such drugs include aspirin, acetaminophen, ibuprofen, and naproxen, among others. For the present application a preferred analgesic is acetaminophen.

The term "clear" as used herein with regard to the inventive fill compositions, means transparent, without any cloudiness or precipitation.

The term "ionizing agent" herein refers to a compound that can react with acetaminophen in the solvent system to form acetaminophen ions. Examples of an ionizing agent include both organic and inorganic bases capable of accepting hydrogen ions or donating electron pairs. Alkali or alkaline-earth metal salts or hydroxides are commonly used ionizing agents to increase the solubility of acetaminophen.

An ionizing agent can be added to the formulation to boost the solubility of acetaminophen in the solvent system. However, it can undesirably accelerate the degradation of acetaminophen. Thus, an acetaminophen formulation having an ionizing agent might be less stable. Based on the required shelf life of a formulation, a person skilled in the art can easily decide whether or not to include an ionizing agent in the formulation. In the formulation of this invention that does not include an ionizing agent, acetaminophen is dissolved at an unexpectedly high concentration in the solvent system, which, as pointed out above, contains polyvinylpyrrolidone, polyethylene glycol, and water.

The term "dissolving" herein means "evenly dispersing an active ingredient (e.g., acetaminophen) as molecules in the solvent system containing polyvinylpyrrolidone, polyethylene glycol, and water for at least three days, as judged by the naked eye or by a magnifying optical device based on two criteria: (i) transparence of the solution, and (ii) no formation of solid precipitation."

The transitional phrase "consisting essentially of" or "consists essentially of" as used herein limits the scope of a claim to the specified materials or steps and those that do not materially affect the basic and novel characteristics of the claimed invention.

One embodiment of the invention is directed to a clear bioavailable liquid softgel fill composition comprising: (a1) acetaminophen as active ingredient; (a2) one or more additional active ingredients selected from the group consisting of dextromethorphan and pharmaceutically acceptable salts thereof; doxylamine and pharmaceutically acceptable salts thereof; guaifenesin; chlorpheniramine and pharmaceutically acceptable salts thereof; and phenylephrine and pharmaceutically acceptable salts thereof; (b) a matrix comprising: about 20-70 wt % (about 20-60, about 20-50, about 30-60, about 30-50, about 40-60, about 45-60, about 40-50, about 45-50, about 45-55, about 47-48 wt %) of a pharmaceutically acceptable poly(alkylene glycol) or mixture of poly(alkylene glycol)s, and about 0.5-8 wt % (about 1-6, about 1-5, about 1.3-5, about 2-6, about 2-5, about 2-4, about 2-3.8 wt %) of a pharmaceutically acceptable alkylene glycol; and (c) a solubilizing agent comprising: about 1-30 wt % (about 1-20, about 1-10, about 2-10, about 3-10, about 2-9, about 2-8, about 3-8, about 3-7 wt %) of a pharmaceutically acceptable polymeric solubilizing agent, and about 1-10 wt % (about 2-9, about 3-8, about 4-7, about 5-7, about 5.5-6.8, about 5-6 wt %) by weight water; where the wt % values are based on the total weight of the composition, and where the fill composition is clear. In one embodiment the clear bioavailable liquid softgel fill composition comprises about 10 to about 60 wt % (about 20-40, about 20-31, about 22-30, about 22.7 or 22.8-28, about 22.7 or 22.8-25 wt %) acetaminophen, about 0.3 to about 3 wt % (about 0.5-2, about 0.6-1, about 0.7-0.9, about 0.7-0.8 wt %) dextromethorphan HBr, 0 to about 2 wt % (e.g., about 0-1.0, about 0.4-0.6, and about 0.5 wt %) doxylamine succinate, 0 to about 30 wt % (about 1-30, about 5-25, about 10-20, about 12-16, about 14-15 wt %) guaifenesin, 0 to about 0.5 wt % (e.g., about 0.1-0.4, about 0.4-0.6, and 0.2 wt %) chlorpheniramine maleate, and about 0.1 to about 2 wt % (about 0.1-1, about 0.2-0.8, about 0.3-0.6, about 0.3-0.4, about 0.37-0.4 wt %) phenylephrine HCl. In another embodiment the clear bioavailable liquid softgel fill composition comprises about 20 to about 31% acetaminophen, about 0.5 to about 1.2 wt % dextromethorphan HBr, 0 to about 1 wt % doxylamine succinate, about 10 to about 20 wt % guaifenesin, 0 to about 0.5 wt % chlorpheniramine maleate, and about 0.1 to about 0.8 wt % phenylephrine HCl. In yet another embodiment the clear bioavailable liquid softgel fill composition comprises about 22 to about 28 wt % acetaminophen, about 0.7 to about 0.9 wt % dextromethorphan HBr, 0 to about 0.6 wt % doxylamine succinate, about 14 to about 15 wt % guaifenesin, 0 to about 0.3 wt % chlorpheniramine maleate, and about 0.3 to about 0.5 wt % phenylephrine HCl. In some embodiments of the clear bioavailable liquid softgel fill composition the active ingredients are limited to acetaminophen, dextromethorphan HBr, guaifenesin, and phenylephrine HCl.

Another aspect of the invention is directed to a clear bioavailable liquid softgel fill composition consisting essentially of: (a1) about 22 to about 25 wt % acetaminophen; (a2) about 0.7 to about 0.8 wt % dextromethorphan HBr; (a3) about 14 to about 15 wt % guaifenesin; (a4) about 0.3 to about 0.4 wt % phenylephrine HCl; (b) a matrix consisting essentially of: about 47 to about 48 wt % of a pharmaceutically acceptable poly(alkylene glycol) or mixture of poly (alkylene glycol)s; and about 2 to about 4 wt % of a pharmaceutically acceptable alkylene glycol; and (c) a solubilizing agent consisting essentially of: about 3 to about 7 wt % of a pharmaceutically acceptable polymeric solubilizing agent; and about 5 to about 6 wt % water; where the wt % values are based on the total weight of the composition, and where the fill composition is clear. In one embodiment of the clear fill composition the pharmaceutically acceptable poly (alkylene glycol) is selected from the group consisting of PEG 400, PEG 600 and mixtures thereof; the pharmaceutically acceptable alkylene glycol is propylene glycol; and the pharmaceutically acceptable polymeric solubilizing agent is polyvinylpyrrolidone. One embodiment of the clear fill composition consists essentially of about 48% PEG 400, about 3.5% propylene glycol, about 4.6% polyvinylpyrrolidone K30, about 6% water, about 22.8% acetaminophen, about 0.7% dextromethorphan HBr, about 14% guaifenesin and about 0.4% phenylephrine HCl.

In a further aspect of the invention the clear bioavailable liquid softgel fill compositions can further contain an anti-oxidant. In some embodiments the anti-oxidant is selected from the group consisting of BHA, BHT and mixtures thereof.

Another aspect of the invention is directed to a softgel capsule comprising a soft gelatin shell filled with any one of the above clear bioavailable liquid softgel fill compositions.

Yet another aspect of the invention is directed to a softgel capsule which comprises: a soft gelatin shell, and a clear liquid softgel fill composition within the shell, the liquid softgel fill composition including: (a1) about 22 to about 25 wt % acetaminophen; (a2) about 0.7 to about 0.8 wt % dextromethorphan HBr; (a3) about 14 to about 15 wt % guaifenesin; (a4) about 0.3 to about 0.4 wt % phenylephrine HCl; (b) a matrix consisting essentially of: about 47 to about 48 wt % of a pharmaceutically acceptable poly(alkylene glycol) or mixture of poly(alkylene glycol)s; and about 2 to about 4 wt % of a pharmaceutically acceptable alkylene glycol; and (c) a solubilizing agent consisting essentially of: about 3 to about 7 wt % of a pharmaceutically acceptable polymeric solubilizing agent; and about 5 to about 6 wt % water, where the wt % values are based on the total weight of the composition, and where the fill composition is clear. One embodiment of the softgel capsule is directed to shell containing a fill composition where the pharmaceutically acceptable poly(alkylene glycol) is selected from the group consisting of PEG 400, PEG 600 and mixtures thereof; the pharmaceutically acceptable alkylene glycol is propylene glycol; and the pharmaceutically acceptable polymeric solubilizing agent is polyvinylpyrrolidone. In another embodiment of the softgel capsule, the fill composition consists essentially of about 48% PEG 400, about 3.5% propylene glycol, about 4.6% polyvinylpyrrolidone K30, about 6% water, about 22.8% acetaminophen, about 0.7% dextromethorphan HBr, about 14% guaifenesin and about 0.4% phenylephrine HCl. In some embodiments of the softgel capsule the total amount of acetaminophen encapsulated is 200-500 mg, 250-400 mg, 300-350 mg, such as 325 mg. In other embodiment the total amount of guaifenesin encapsulated is 100-300 mg, 150-250 mg, such as 200 mg.

Another aspect of the invention is directed to a method of preparing a clear liquid softgel fill composition as disclosed above, where method comprises: a) stirring polyethylene glycol or a mixture of polyethylene glycols, and propylene glycol with heating to 70° C.±10° C. until a clear solution is obtained; b) slowly adding polyvinylpyrrolidone in small quantities with continuous mixing and heating to 70° C.±10° C., until a clear solution is obtained; c) adding purified water with continuous mixing and heating to 70° C.±10° C., until a clear solution is obtained; d) adding acetaminophen with continuous mixing and heating to 70° C.±10° C., until a clear solution is obtained; e) adding guaifenesin with continuous mixing and heating to 70° C.±10° C., until a clear solution is obtained; f) successively adding i) dextromethorphan HBr and ii) phenylephrine HCl with continuous mixing and optionally heating up to 80° C., until a clear solution is obtained; and g) cooling to ambient temperature and deaerating the clear liquid softgel fill solution. In some embodiment of the method the polyethylene glycol is selected from the group consisting of PEG 400, PEG 600 and mixtures thereof. In some embodiments of the method the temperature of the solution during the addition of dextromethorphan HBr is up to 55° C., and the temperature of the solution during the addition of phenylephrine HCl is below 35° C.

The liquid softgel fill formulation can be encapsulated in soft gelatin shells to form softgel capsules, for example by using a conventional rotary die process. Suitable soft gelatin shells may include (i) gelatin, 20-60% by weight; (ii) glycerin, 0-30% by weight; (iii) sorbitol, 0-30% by weight; (iv) purified water, 20-50% by weight; and (v) artificial color, 0.0001-0.002% by weight. The highly concentrated solution of active ingredients found in the liquid softgel fill formulations of the present invention allows the entire combination to be encapsulated into a reasonably small sized (0.2-1.8 mL) clear softgel capsule for easy swallowing. The inventive formulation also enhances the bioavailability of the active ingredients. Further, encapsulation of the ingredients masks the negative taste of the active ingredients so that compliance issues with taking the medication are minimized.

The softgel capsules of the invention can also be prepared by other methods well known in the art. See e.g., P. K. Wilkinson et al., "Softgels: Manufacturing Considerations," Drugs and the Pharmaceutical Sciences, 41 (Specialized Drug Delivery Systems); P. Tyle, Ed. (Marcel Dekker, Inc., New York, 1990) 409-449; F. S. Hom et al., "Capsules, Soft" Encyclopedia of Pharmaceutical Technology, vol. 2; J. Swarbrick and J. C. Boylan, eds. (Marcel Dekker, Inc., New York, 1990) pp. 269-284; M. S. Patel et al., "Advances in Softgel Formulation Technology," Manufacturing Chemist, vol. 60, no. 7, pp. 26-28 (July 1989); M. S. Patel et al., "Softgel Technology," Manufacturing Chemist, vol. 60, no. 8, pp. 47-49 (August 1989); R. F. Emerson, "Softgel (Soft Gelatin Capsule) Update," Drug Development and Industrial Pharmacy (Interphex '86 Conference), vol. 12, no. 8 & 9, pp. 1133-1144 (1986); and W. R. Ebert, "Soft Elastic Gelatin Capsules: A Unique Dosage Form," Pharmaceutical Technology, vol. 1, no. 5, pp. 44-50 (1977).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4.

Polyvinylpyrrolidone, also known as Polyvidone or Povidone, is a water-soluble polymer. Polyvinylpyrrolidone used in this invention has an molecular weight in the range of 2,000 to 1,500,000, e.g., 2,000 to 62,000, 2,000 to 4,000, 4,000 to 18,000, or 6,000 to 15,000. Polyvinylpyrrolidone products are commonly graded by K values. The K value is an index for correlating relative viscosity with the average degree of polymerization. See Cellulose Chem. 1932, 13, 60. The K value is calculated by the following formula:

$$K = (1.5 \log \eta_{rel} - 1)/(0.15 + 0.003c) + (300c \log \eta_{rel} + (c + 1.5c \log \eta_{rel})^2)^{1/2}/(0.15c + 0.003c^2)$$

$\eta_{rel}$: Relative viscosity of aqueous polyvinylpyrrolidone solution to water. c: Content of polyvinylpyrrolidone in an aqueous polyvinylpyrrolidone solution (w/w %).

Polyvinylpyrrolidone used in the formulation has a K value of 12 to 90, e.g., 12, 15, 17, 25, or 30. Polyvinylpyrrolidone is designated as Povidone in the United States Pharmacopeial Convention ("USP"). Polyvinylpyrrolidone products are commercially available and generally include K values in their trade names, e.g., Polyvinylpyrrolidone K17 or Povidone K17. There are correlations between K values and molecular weights. For example, polyvinylpyrrolidone K12 has a molecular weight of 2,000 to 4,000, K15 6,000 to 15,000, K17 4,000 to 18,000, K30 40,000 to 62,000, and K90 1,000,000 to 1,500,000. Polyvinylpyrrolidone products from different vendors may have different average molecular weights, which typically fall into the ranges cited above.

Polyvinylpyrrolidone herein refers to a single product or a mixture of several products. For example, it can be polyvinylpyrrolidone K12, K15, K17, K25, K30, K60, K90, or a mixture thereof. Polyvinylpyrrolidone enhances the solubility of AIs in the solvent system containing polyvinylpyrrolidone, polyethylene glycol, water, and optionally propylene glycol or other components.

Polyethylene glycol, also known as "PEG," has a formula of $H(OCH_2CH_2)_nOH$, wherein n is 4 or greater. A number generally follows the name PEG to indicate its average molecular weight. For example, PEG-400 has an average molecular weight of about 400. See Cosmetic Ingredient Dictionary, 3d Ed. (1982), pages 201-03; Merck Index, 10th Ed. (1983), page 1092.

Polyethylene glycol used in this invention is a clear viscous liquid or a white solid at room temperature, and can be dissolved in water and many organic solvents. Its molecular weight can be between 200 and 800, preferably 400-600. The solvent system can contain a single polyethylene glycol product or a mixture of two or more polyethylene glycol products.

EXAMPLES

Example 1. Bioavailable Fill Composition with Fexofenadine Hydrochloride as Active Ingredient Formula of Example 1:

| Ingredient | Function | Range (wt %) |
| --- | --- | --- |
| PEG 400, PEG 600, or mixtures | Matrix | 40-55 |
| Propylene Glycol | (part A) | 1-5 |
| Polyvinylpyrrolidone: PVP K12, PVP K17, PVP K30, or mixtures | Solubilizing Agent | 5-20 |
| Water | (Matrix, part B) | 1-10 |
| Analgesic | Active Ingredient | Remainder to 100 |
| Decongestant, Expectorant, Antitussive and/or antihistamine | Active Ingredient | 100 |

All ingredients were mixed according to the procedure of Example 2.

Example 2. Process for Preparation of Fill Composition of Examples 1, 3 and 4 a) Add Propylene Glycol into PEG 400 and/or PEG 600 in a suitable stainless steel container. Heat the solution to 70° C.±10° C. Use a Stainless Steel Propeller/High Shear Mixer to mix all ingredients for 30±5 minutes or until homogenized.
b) Slowly add PVP K12 (or PVP K17, or PVP K30, or mixtures) in small quantities to solution a) while continuously mixing at 70° C.±10° C. Mix thoroughly for additional 30±5 minutes after powder addition has been completed.
c) Add Water. Continue to mix at 70° C.±10° C. for additional 15±2 minutes or until homogenized.
d) Add active ingredients into solution in small quantities while continuing to mix at 70° C.±10° C. Mix for additional 45±5 minutes after powder addition has been completed.
e) Cool solution to room temperature and deaerate.

Encapsulate the above suspension into a soft gelatin capsule (softgel). Optionally, the softgel capsules are then provided with an enteric coating consisting of hydroxypropyl methyl cellulose stearate and castor oil as plasticizer, in the customary manner.

Example 3. Bioavailable Fill Composition Containing Acetaminophen, Dextromethorphan, Doxylamine Succinate and Phenylephrine Formula of Example 3:

| Ingredient | Function | wt % |
| --- | --- | --- |
| PEG 400 and/or 600 | Matrix | 48 |
| Propylene Glycol | (part A) | 1.3 |
| Polyvinylpyrrolidone: PVP K12 or K17 or K30 | Solubilizing Agent | 14 |
| Water | (Matrix, part B) | 6.3 |
| Acetaminophen | Active Ingredient | 28 |
| Dextromethorphan HBr | Active Ingredient | 0.9 |
| Doxylamine Succinate | Active Ingredient | 0.5 |
| Phenylephrine HCl | Active Ingredient | 0.5 |

All ingredients were mixed according to the procedure of Example 2.

Example 4. Bioavailable Fill Composition Containing Guaifenesin, Acetaminophen, Dextromethorphan and Phenylephrine Formula of Example 4:

| Ingredient | Function | wt % |
| --- | --- | --- |
| PEG 400 and/or 600 | Matrix | 47 |
| Propylene Glycol | (part A) | 2 |
| Polyvinylpyrrolidone: PVP K12 or K17 or K30 | Solubilizing Agent | 7 |
| Water | (Matrix, part B) | 6 |
| Acetaminophen | Active Ingredient | 23 |
| Dextromethorphan HBr | Active Ingredient | 0.7 |
| Guaifenesin | Active Ingredient | 14 |
| Phenylephrine HCl | Active Ingredient | 0.4 |

All ingredients were mixed according to the procedure of Example 2.

See FIG. 1 which shows a picture of a sample of the composition of Example 4 after storage for 2 years. After this time the sample remained clear.

The clear fill composition of Example 4 (1426 mg) was encapsulated to provide a clear softgel capsule containing 325 mg acetaminophen and 200 mg guaifenesin plus dextromethorphan and phenylephrine.

Example 5. Bioavailable Fill Composition Containing Guaifenesin, Acetaminophen, Dextromethorphan and Phenylephrine In this example, a bioavailable fill composition containing guaifenesin was prepared according to the following formula and process.

Formula of Example 5:

| Ingredient | Percentage (wt %) |
| --- | --- |
| PEG 600 | 15 |
| PEG 400 | 32 |
| PVP K30 | 3 |
| Propylene glycol | 3.8 |
| Water | 5.6 |
| Acetaminophen | 25 |
| Dextromethorphan HBr | 0.8 |
| Guaifenesin | 15 |
| Phenylephrine HCl | 0.4 |

Process of Example 5:
1. Add PEG 400, Propylene glycol and PEG 600 to a beaker, heat to 60-80° C., mix for 15 minutes until clear.
2. Add PVP K30, heat to 60-80° C., mix for 30-60 minutes until clear.
3. Add water, heat to 60-80° C., mix for 10 minutes until clear.
4. Add acetaminophen, heat to 60-80° C., mix for 20-50 minutes until clear.
5. Add guaifenesin, heat to 60-80° C., mix for 20-40 minutes until clear.
6. Add dextromethorphan HBr and phenylephrine HCl, heat to 60-80° C., mix for 20-60 minutes until clear.

Example 6. Bioavailable Fill Composition Containing Acetaminophen, Guaifenesin, Dextromethorphan and Phenylephrine In this example, a bioavailable fill composition containing guaifenesin was prepared according to the following formula and process.

Formula of Example 6:

| Ingredient | % w/w |
| --- | --- |
| PEG 400 | 48 |
| Propylene glycol (PG) | 3.5 |
| PVP K29-32 (K30) | 4.6 |
| Purified Water | 6 |
| Acetaminophen | 23 |
| Dextromethorphan HBr | 0.7 |
| Guaifenesin | 14 |
| Phenylephrine HCl | 0.4 |

Process of Example 6:
1. Weigh accurately required amount of PEG 400 and PG and transferred in to Glass beaker.
2. Add only 94% of DI water to step 1 and Mix for 10 min. Keep remaining 6% of DI water aside.
3. Weigh accurately required amount of PVP K29-32 and transfer it to step 2 and mix until it becomes clear.
4. Turn on the heat and allow mixture to heat to 70° C.
5. Weigh accurately required amount of acetaminophen and transfer to pre-heated mixture gradually and mix until it becomes clear.
6. Weigh accurately required amount of guaifenesin and mix it into step 5 until it becomes clear. Lower the heat to 55° C.
7. Weigh accurately required amount of dextromethorphan HBr and mix it into step 6 until it becomes clear. Turn off the heat and wait till mixture temperature is below 35° C.
8. Weigh accurately required amount of phenylephrine HCl and add remaining amount of water to the mixture. Mix until it becomes clear.
9. Place the fill solution under vacuum to deaerate and remove the bubbles.

Example 7. Bioavailable Fill Composition Containing Acetaminophen, Dextromethorphan, Chlorpheniramine and Phenylephrine Formula of Example 7:

| Ingredient | Percentage (wt %) |
| --- | --- |
| PEG 600 | 39 |
| PEG 400 | 18 |
| PVP K30 | 3.4 |
| Propylene glycol | 5 |
| Water | 6.7 |
| Anti-oxidant (BHA/BHT) | 0.04 |
| Acetaminophen | 27 |
| Dextromethorphan HBr | 0.9 |
| Chlorpheniramine Maleate | 0.2 |
| Phenylephrine HCl | 0.4 |

Process of Example 7:
1. Pre-weight all ingredients of formula into separate clean stainless steel containers.
2. Charge Polyethylene Glycol 400, Polyethylene Glycol 600 and Propylene Glycol into a suitable container equipped with mixer. Slowly mix for 15 minutes at 70° C.±5° C.
3. Add BHT to the above glycol solution. Continue to mix at 70° C.±5° C. for another 10-15 minutes.
4. Add BHA to the solution. Continue to mix at 70° C.±5° C. for another 10-15 minutes.
5. Slowly add Povidone K-30 into the solution above. Continue to mix at 70° C.±5° C. for another 20-30 minutes or until clear solution.
6. Add Purified water into the solution above. Continue to mix at 70° C.±5° C. for another 10 minutes.
7. Slowly add Acetaminophen into the solution above. Continue to mix at 70° C.±5° C. for another 20-30 minutes or until all completely dissolved and clear.
8. Slowly add Chlopheniramine Maleate into the solution above. Continue to mix at 70° C.±5° C. for another 15-20 minutes or until all completely dissolved and clear.
9. Slowly add Dextromethorphan HBr into the solution above. Continue to mix at 70° C.±5° C. for another 15-20 minutes or until all completely dissolved and clear.
10. Slowly add Phenylephrine HCl into the solution above. Continue to mix at 70° C.±5° C. for another 15-20 minutes or until all completely dissolved and clear.
11. Stop mixing. Deaerate solution. Blanket the solution with nitrogen until encapsulation.

The specific examples disclosed above are to be construed as merely illustrative, and not limitative of the remainder of the disclosure in any way whatsoever. Without further elaboration, it is believed that one skilled in the art can, based on the description herein, utilize the present invention to its fullest extent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the present claims.

All publications cited herein are hereby incorporated by reference in their entirety.

What is claimed is:

1. A method of preparing a clear liquid softgel fill composition consisting of the steps of:
   a) stirring polyethylene glycol or a mixture of polyethylene glycols, and propylene glycol with heating to 70° C.±10° C. until a clear solution is obtained; followed by
   b) slowly adding polyvinylpyrrolidone in small quantities with continuous mixing and heating to 70° C.±10° C., until a clear solution is obtained; followed by
   c) adding purified water with continuous mixing and heating to 70° C.±10° C., until a clear solution is obtained; followed by
   d) adding acetaminophen in small quantities with continuous mixing and heating to 70° C.±10° C., until a clear solution is obtained; thereafter
   e) adding guaifenesin with continuous mixing and heating to 70° C.±10° C., until a clear solution is obtained;
   f) successively adding i) dextromethorphan HBr and ii) phenylephrine HCl with continuous mixing and optionally heating up to 80° C., until a clear solution is obtained; and
   g) cooling to ambient temperature and deaerating the clear solution from step f;
   whereby said clear liquid softgel fill composition is stable to storage for at least two years,
   wherein steps a) to g) are performed in a single container and in an order as set forth above.

2. The method of claim 1, wherein the polyethylene glycol is selected from the group consisting of PEG 400, PEG 600, and mixtures thereof.

3. The method of claim 1, wherein the temperature of the solution during the addition of dextromethorphan HBr is up to 55° C., and the temperature of the solution during the addition of phenylephrine HCl is below 35° C.

* * * * *